(12) United States Patent
Longo

(10) Patent No.: US 11,324,578 B2
(45) Date of Patent: May 10, 2022

(54) DRAINING BIOLOGICAL PATCH

(71) Applicant: ASSUT EUROPE SPA, Rome (IT)

(72) Inventor: Maurizio Longo, Rome (IT)

(73) Assignee: ASSUT EUROPE SPA, Rome (IT)

(*) Notice: Subject to any disclaimer, the term of this patent is extended or adjusted under 35 U.S.C. 154(b) by 149 days.

(21) Appl. No.: 16/461,101

(22) PCT Filed: Nov. 29, 2017

(86) PCT No.: PCT/IB2017/001789
§ 371 (c)(1),
(2) Date: May 15, 2019

(87) PCT Pub. No.: WO2018/146510
PCT Pub. Date: Aug. 16, 2018

(65) Prior Publication Data
US 2019/0358017 A1  Nov. 28, 2019

(30) Foreign Application Priority Data
Nov. 30, 2016 (IT) .......................... 102016000120887

(51) Int. Cl.
*A61F 2/00* (2006.01)
*A61L 27/24* (2006.01)
*A61F 2/12* (2006.01)

(52) U.S. Cl.
CPC ............ *A61F 2/0063* (2013.01); *A61L 27/24* (2013.01); *A61F 2/12* (2013.01);
(Continued)

(58) Field of Classification Search
CPC .. A61F 2/0063; A61F 2/12; A61F 2002/0068; A61F 2230/0008;
(Continued)

(56) References Cited

U.S. PATENT DOCUMENTS 9,901,440 B2 *  2/2018  Liu .......................... A61F 2/12
10,537,665 B2 *  1/2020  Ringo .................... A61L 27/362
(Continued)

FOREIGN PATENT DOCUMENTS

EP  1 389 450  2/2004
EP  3 034 038  6/2016
(Continued)

OTHER PUBLICATIONS

Klinge, U. et al., "Veränderung der Bauchwandmechanik nach Mesh-Implantation, Experimentelle Veränderung der Mesh-Stabilität," Langenbecks Arch Chir, vol. 381, 1996, pp. 323-332.
(Continued)

*Primary Examiner* — Jerrah Edwards
*Assistant Examiner* — Mihret Tafesse
(74) *Attorney, Agent, or Firm* — Nixon & Vanderhye P.C.

(57) ABSTRACT

The present invention relates to an innovative biological prostheses, equipped with a drainage system, designed for all surgical applications where there is any risk of hematomas or seromas, which not only allows to minimize adverse events arising from its application, but allows also to improve the effectiveness of the functional reconstruction. The prosthesis of the present invention is a surgical prosthesis made of animal derived collagen having a peripheral outline and a drainage portion comprising a plurality of drainage holes which are located in one or more independent groups each of which has a regular body-centered polygon layout.

24 Claims, 4 Drawing Sheets

Figure 1:
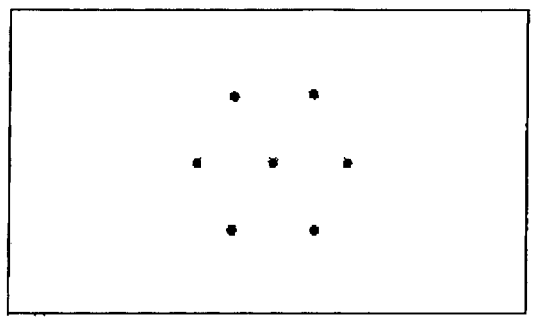

(52) U.S. Cl.
CPC ........... *A61F 2002/0068* (2013.01); *A61F 2230/0008* (2013.01); *A61F 2230/0015* (2013.01); *A61F 2230/0019* (2013.01); *A61F 2250/0014* (2013.01)

(58) Field of Classification Search
CPC ...... A61F 2230/0015; A61F 2230/0019; A61F 2250/0014; A61F 2250/0023; A61L 27/24
See application file for complete search history.

(56) References Cited

U.S. PATENT DOCUMENTS

| | | | |
|---|---|---|---|
| 2004/0034374 A1* | 2/2004 | Zatzsch | A61F 2/0063 606/151 |
| 2011/0022171 A1 | 1/2011 | Richter et al. | |

FOREIGN PATENT DOCUMENTS

| | | |
|---|---|---|
| WO | WO 99/16381 | 4/1999 |
| WO | WO 2008/016919 | 2/2008 |
| WO | WO 2010/071624 | 6/2010 |
| WO | WO 2015/065923 | 5/2015 |
| WO | WO 2017/044682 | 3/2017 |

OTHER PUBLICATIONS

Montgomery, "The Battle Between Biological and Synthetic Meshes in Ventral Hernia Repair," Hernia, vol. 17, 2013, pp. 3-11.
Tutomesh® Soft Tissue Replacement with Tutomesh® an Avital, Acellular Xenogenic Collagen Membrane Brochure, Tutogen Medical GmbH, Mar. 1, 2013, 8 pp.
Urbach, V. et al., Bovines Perikard Anwendungstechnikenbeideroperativen Versorgung von Hernien, Biomaterialien, vol. 8 (S1), 2007, pp. 82-83 (Meeting Abstract, Deutsche Gesellschaft für Chirurgie. 125. Kongress der Deutschen Gesellschaft für Chirurgie, Berlin, Apr. 22-25, 2008 and English translation, 3 pp.).
Zhu, Lei-Ming et al., "Mesh Implants: An Overview of Crucial Mesh Parameters," World Journal of Gastrointestinal Surgery, vol. 7, No. 10, Oct. 27, 2015, pp. 226-236.
International Search Report dated Oct. 31, 2018 issued in PCT International Patent Application No. PCT/IB2017/001789, 6 pp.

* cited by examiner

DRAINING BIOLOGICAL PATCH

This application is the U.S. national phase of International Application No. PCT/IB2017/001789 filed Nov. 29, 2017 which designated the U.S. and claims priority to Italian Patent Application No. 102016000120887 filed Nov. 29, 2016, the entire contents of each of which are hereby incorporated by reference.

TECHNICAL FIELD OF THE INVENTION

The present invention relates to an innovative biological prosthesis, equipped with a drainage system, designed for all surgical applications where there is any risk of hematoma or seroma formation, which not only allows to minimize the adverse events resulting from its application, but also allows to improve the effectiveness of functional reconstruction

BACKGROUND

Biological prostheses are mainly used in reconstructive surgery of the abdominal wall, but their use is also developing in dental surgery, cosmetic surgery, reconstructive surgery, cancer surgery and breast surgery.

Talking about the abdominal wall, the abdomen is the region of the body located between thorax and pelvis, whose walls delimit a cavity containing most of the organs of the digestive, urinary and genital apparatus. The abdominal band muscles protect the viscera and help maintain or increase abdominal pressure. They participate in the movement of the trunk and maintain body posture. The rectus muscles come into play when the subject attempts to bend; oblique and transverse muscles increase intra-abdominal pressure and are therefore important in breathing, defecation, child birth, etc. One of the main problems of the abdominal wall is the formation of hernias that occurs when a viscera or part of it comes out through a natural orifice that should contain it. It most commonly occurs in the inguinal regions (in women it is prevalent in the crural space), femoral and umbilical.

Umbilical hernias are often congenital and result from an incomplete closure of the abdominal wall. Ventral hernia may be occurring through defects or weaknesses in the alba line or along the semilunar line. In some cases there may be the formation of a postoperative hernia on a surgical incision, called "laparocele".

The hernia must be operated as it is an irreversible anatomical lesion and therefore tends to enlarge, sometimes enormously, or complicate with the throttling of the entrails contained and with the gangrene: it is very serious when the intestine is throttled. Many of the incisional hernias can be repaired with a simple closure or extrapolation of the same, with consequent suture of the created wound. However where the flaw is relatively large or if the closure may remain in a condition of stress, it becomes necessary to the insertion of prosthetic materials. Also, increasingly, to prevent the recurrence of the hernia or incisional hernia, even when in the first instance would not be strictly necessary the hernia is repaired with the use of synthetic or biological prosthesis.

Classical techniques for the reconstruction of defects around the abdomen include the use of synthetics and myocutaneous flaps. In these cases often occurred complications such as wound Infection and lack of growth of tissue around the synthetic mesh (prosthesis) that can lead to a new formation of hernia or necrosis around the edges. Incisional hernias cause complications on more than 20% of patients who have previously had a laparotomy. Despite the progress made with the use of surgical implants, any synthetic mesh used in the abdominal wall may cause complications with infections present in 5-30% of cases, which is why, we observe an ever wider use of biological prosthesis.

Of considerable importance are also applications in surgical oncology and breast reconstruction and will be even more in the future as it Is expected an increase in new cases of breast cancer for the next decades, from about 45,000 of 2014 we expect approximately 49,000 new cases for 2020 (+9.6%) and more than 51,500 new cases for 2030 (+15.6%). Breast cancer, which for women is the first cause of death from cancer, is in first place even with different age groups, accounting for 30% of causes of death of cancer before the age of 50 years, 21% between 50 and 69 years and 13% after 70 years, Relative survival at 5 years is moderate and steady increase for many years (81% for sick women from 1990 to 1994, 85% from 1995 to 1999, 87% from 2000 to 2004), depending on several variables, including screening and diagnostic anticipation and improvement of therapies. However in Oncology, breast cancer survival and disease-free interval is no longer the only objectives to be pursued: lately, in fact, the concept of quality of life is taking increasingly importance. It is strongly influenced by the physical integrity and the body Image that the subject has of himself. For this reason, in women who underwent a mastectomy for breast cancer, breast reconstruction has become an integrated part in the therapeutic process, being required by a growing number of patients.

In recent years we are observing an increasing use of biological scaffolds in post-mastectomy breast reconstruction. In this context the use of collagen implants allows immediate breast reconstruction with favorable psychological impact on the patient, as well as a lower overall cost of surgical therapy of breast cancer.

Among the possible uses described above, the ideal biomaterial for use by applications on soft tissues should be able to provide adequate correction thanks to a high mechanical resistance, look natural, not give body reactions and last but not least be able to allow proper drainage of hematomas and seromas, if any (blood or fluid buildup, respectively) that can form in the postoperative.

About it when a prosthesis is inserted Into the body it Is Important to know which tissues will go to replace and which stresses/strains will be submitted. Engineering studies have been carried out in this area to determine the efforts and flexibility that characterize the different areas of application.

As reported in the study of literature of Prof. Klinge (June 1996 Alteration of abdominal wall mechanics after implantation mesh. Experimental alteration of mesh stability. LangenbecksArchChlr; 381, 323-332), it has been shown that the Implants currently on the market are too strict because their tensile strength exceeds by 16 N/cm physiological needed value.

With regard to the application of biological Implants in breast reconstruction, in addition to the structural function that recreates an "internal bra", it must ensure an aesthetic result providing extra tissue for the lower bracket of the Implant.

Biological implants exist in many forms, each with its own specific task and microstructure, but all are composed of extracellular matrix.

The properties of these materials does not depend only by animal species and the type of tissue from which they are derived, but also from the industrial process to which they are subject. All biological implants derived from animal tissues undergo a treatment of decellularization to remove native cells from the tissue, which typically is made with chemical or enzymatic processes. Some biological scaffolds are cross-linked to stabilize them artificially. In addition the prostheses are typically contoured and in some instances perforated by reducing the mechanical resistance of the prosthesis itself, and in some cases creating preferential direction of break.

Today a fenestrated prosthesis is widely used (Tutomesh®), it is a collagen membrane permeable to liquids, made from bovine pericardium through a methodical multiphasic processing.

Multiphasic processing "Tutoplast®" consists in thorough cleansing of the membrane and in a delicate chemical dehydration. This process ensures inactivation of pathogens, without alteration of the three-dimensional structure of collagen and its biomechanical properties. Tutomesh® presents a distribution of drainage holes according to a homogeneous square matrix over the entire surface of the prosthesis that Is available in various shapes and sizes. The drainage holes have a diameter of 1 mm, separated from each other by a distance of 1 cm. The distribution of the outermost holes expected to be 1 cm away from the edges of the prosthesis by producing in this way a constant boundary by which the prosthesis is anchored with a suture.

The use of prosthesis with similar characteristics to the one described above has greatly enhanced post courses cases and the recurrence rate although as stated in the technical is documentation of the occurrence of seromas Tutomesh® is still equivalent to 7.9% of cases (Urbach et al. BovinesPerlkard—Anwendungstechnikenbeideroperativen Versorgung von Hernien, Biomaterialien 2007; Vol 8 (S1): 82-83).

Hematomas or Seromas can form in various regions of the area affected by the intervention in relation to preferential directions followed by fluids. They are also influenced by postoperative hospital stay as it will tend to go into certain areas due to the force of gravity. For this reason, the drainage system developed provides an inhomogeneous distribution on surface and concentrated solely on areas where the fluids tend to accumulate. If hematoma or seroma can't form in some areas a not perforated portion Is preferable in order to maximize the mechanical resistance.

For the same reasons also the distance of the holes from the edge of the implant should not be constant. In this way you would get an outline of the perforated area with large holes-free zones that facilitate safe fastening of prosthesis offering a superior mechanical performance. Always in connection with the not perforated areas, experimental tests have shown that the best results are obtained when we have distances between the holes and the edges of at least 1.5 cm.

Synthetic prosthesis having 1 mm diameter holes was evaluated in several articles of literature (e.g. Klinge et all: _2015 J Gastrointest Surg. 0689 World October 27; 7 (10): 226-236). However the experimental tests carried out in the development of the prosthesis presented in this invention have shown that the size of 1 mm holes isn't sometimes enough. Experimental results of studies performed by the Assut Europe S.p.A. have shown that in order to have an efficient and performant drainage is preferable to have at least 1.5 mm holes. With holes placed at least 1.5 cm distance between them you get better mechanical resistance compared to that observed for example with holes spaced about 1 cm.

Being the prosthesis a scaffold for cell growth, the holes having 1 mm size will seal due to cell engraftment faster than larger ones and therefore they will have a deterioration in the performance of the drainage system. In the light of this observation is possible to assert that holes having at least 1.5 mm dimensions will produce a better drainage function.

Mechanical tests have demonstrated that the optimal disposition of the holes does not have to be of linear type or regular square matrix type in order to avoid the formation of preferred cut directions that can affect the prosthesis breaking resistance.

SUMMARY OF THE INVENTION

The technical problem solved by the present Invention is to supply a biological prosthesis with a performing drainage system that not only concurs to minimize the adverse events deriving from its application, but also allows to improve the effectiveness of the functional reconstruction.

Such problem is solved by biological prostheses described in claim 1.

Preferred characteristics of the present invention are object of the depending claims.

The present Invention concerns a perforated biological prosthesis, preferentially obtained from bovine pericardium or from swine derma, after a multiphasic decellularization processing owned by Assut Europe S.p.A. that does not provide necessarily the use of surfactants and allow an efficient purification of extracellular matrix without affecting the mechanical resistance. Holes are performed to allow effective drainage of hematomas and seromas.

The technical effect over described is generated from an optimized distribution of the holes that in combination with the characteristics of the material of the prosthesis, concur to have suitable mechanical characteristics and permeability.

The biological prosthesis in this way will render sturdier the repair recreating a biological support and contributing to a better drainage of the fluids that will form in the postoperative. The drainage system is realized with a distribution of holes (defined from now in ahead "drainage group") disposed at the vertices and at center of a regular centered body polygon.

In cases in which for specific requirements liquids can potentially accumulate in two or more distinguished areas or a very wide area, 2 or more drainage groups can be realized.

The holes of the drainage group are realized with diameters from at least 1.5 mm and placed to a minimal distance between each other of at least 1.5 cm.

The holes are placed following a not constant distribution from the edges of the prosthesis, but in any case always with one greater or equal distance to 1.5 cm. In this way you get a not perforated outline enabling a more effective fastening of the prosthesis by suturing.

In every drainage group the diameter of the holes can be not constant and the drainage group can be not placed in the central zone of the prosthesis.

Figure 2:
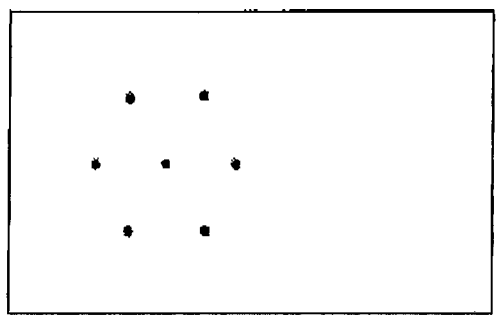
Figure 3:
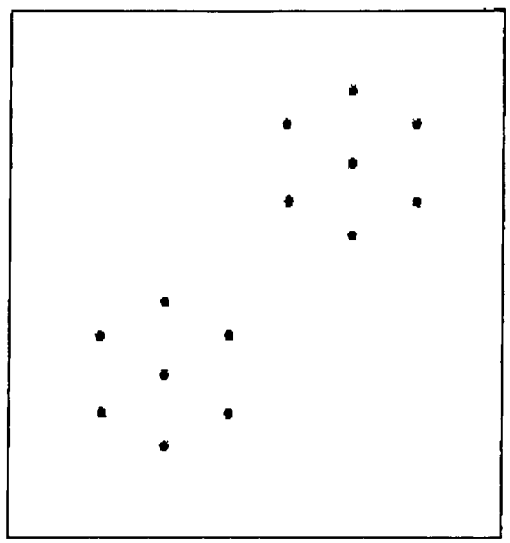
Figure 4:
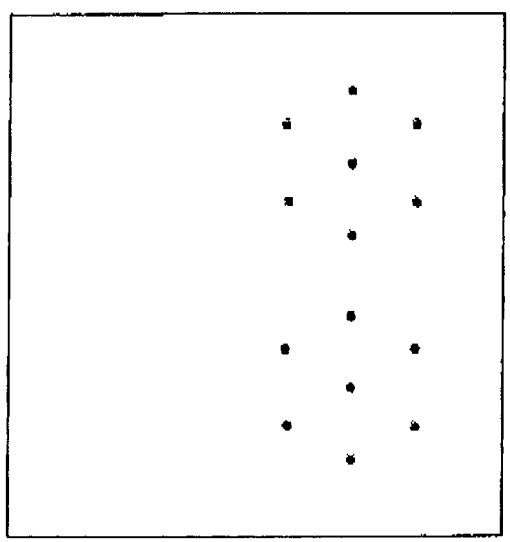
Figure 5:
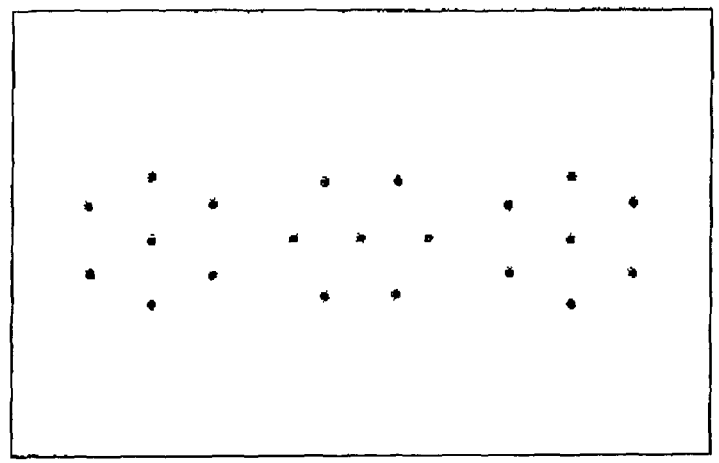
Figure 6:
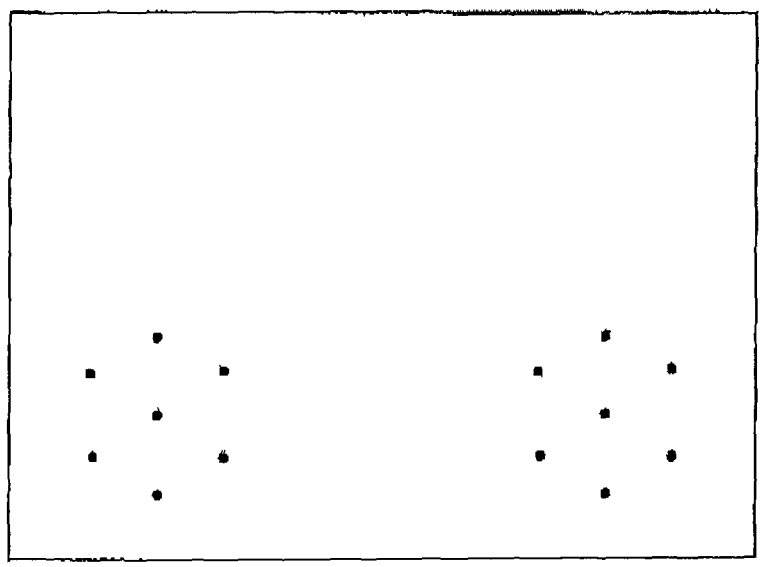
Figure 7:
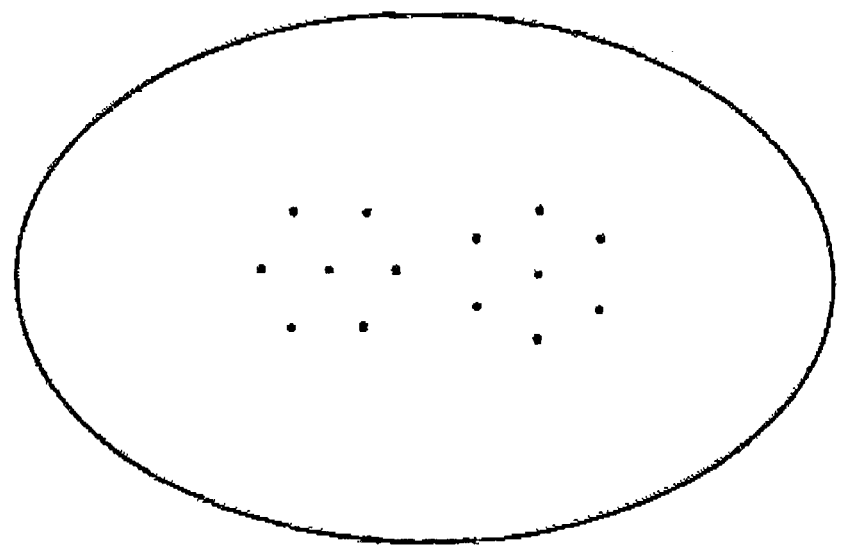
Figure 8:
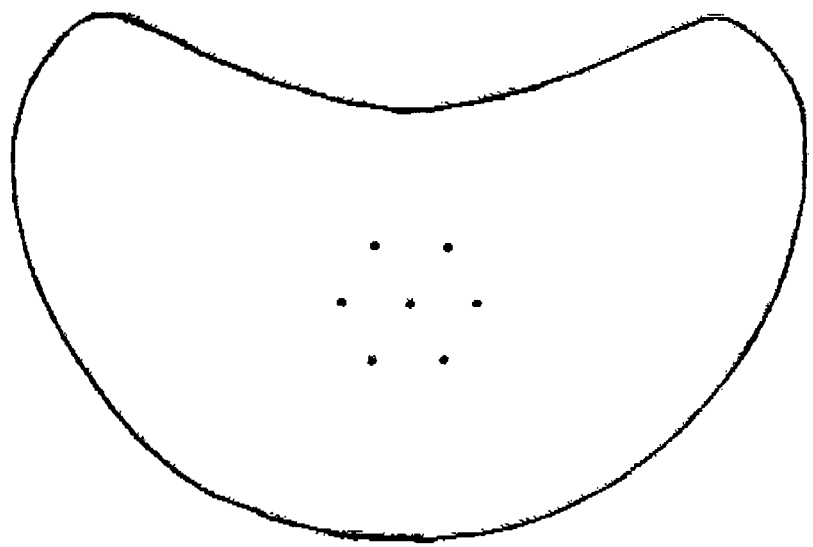

Other advantages, characteristics and the modalities of application of the present Invention will turn out from the following detailed description of some preferred shapes of realization, introduced not for limitative purposes but for exemplifying. Reference is made to the attached drawings, wherein:

the FIG. 1 shows the prosthesis according to an embodiment of the present invention, with one group of drainage placed in a central symmetric position;

the FIG. 2 shows the prosthesis according to an embodiment of the present invention, having one group of drainage placed with a asymmetrically position respect to the center;

the FIG. 3 show the prosthesis in accordance with one embodiment of the present invention with two groups of drainage placed symmetrically respect to the center;

the FIG. 4 show the prosthesis in accordance with one embodiment of the present invention with two groups of drainage placed asymmetrically respect to the center;

the FIG. 5 show the prosthesis in accordance with one embodiment of the present invention with three groups of drainage placed symmetrically respect to the center with one of the two group placed in central position;

the FIG. 6 show the prosthesis in accordance with one embodiment of the present invention with two groups of drainage placed asymmetrically respect to the center;

the FIG. 7 show the prosthesis in accordance with an elliptical shape realization;

the FIG. 8 show the prosthesis in accordance with a "bean shape" realization.

The FIG. 1 shows a prosthesis for surgery with a centered drainage group.

Drainage group is preferentially shaped like a regular body centered hexagon placed at the center of the prosthesis.

In a preferred configuration the drainage group has holes of same dimension. In a more preferred configuration the drainage group has holes with not constant diameter, but however equal at least 1.5 mm and arranged at least 1.5 cm of distance one from the other. Preferentially the prosthesis can have a not perforated contour of at least 1.5 cm. Still more preferentially the external edges can be beveled.

In some preferred shapes of realization the prostheses with beveled edges have rectangular shape and dimensions in mm of 20×20, 40×50, 60×80, 80×90, 80×140, 80×200 with one or more drainage groups.

For other kind of applications, which as an example the mammary surgery, the preferred shapes of realization for prostheses are elliptic or "beam shaped" as in the FIG. 7 and FIG. 8 shown more ahead, having the minimal and maximum dimension respective of 80×160, 100×180 and 120×200 with one or more drainage groups.

Preferentially the drainage groups have a symmetrical disposition respect to the center of the prosthesis. Still more preferentially no drainage group is exactly at the center of the prosthesis. In other preferred embodiments drainage groups can be in an asymmetric position respect to the center of the prosthesis.

Preferentially the asymmetric position of the drainage groups is realized along the greater dimension of the prosthesis.

Still more preferentially all the drainage groups can be found on one side of the bigger axis of the prosthesis.

The invention claimed is:

1. A prosthesis for surgery consisting of animal derived collagen having a peripheral perimeter and a drainage portion within the perimeter provided with a plurality of drainage holes, wherein the holes are placed in one or more groups, and each group has a regular body-centered polygon layout, wherein each group consists of a single hole at a center of the regular body-centered polygon and holes disposed at vertices of the regular body-centered polygon surrounding the single hole without further holes between the single hole and the holes disposed at the vertices and without further holes radially outward of the holes disposed at the vertices, and wherein each group of holes is independent, such that each group does not share any hole with any other group.

2. The prosthesis for surgery according to claim 1 in which the holes have a diameter of 1.5 mm or more, placed at a distance of 1.5 cm or at a greater distance.

3. The prosthesis for surgery according to claim 1 in which the holes have a diameter of 1.5 mm.

4. The prosthesis for surgery according to claim 1 wherein the holes of each group have a body-centered regular hexagon layout.

5. The prosthesis for surgery according to claim 1 in which the groups of holes are placed symmetrically with respect to the center of the prosthesis.

6. The prosthesis for surgery according to claim 1 in which the groups of holes are placed symmetrically with respect to the center of the prosthesis, but without being placed at the center itself.

7. The prosthesis for surgery according to claim 1 in which the groups of holes are placed asymmetrically with respect to the center of the prosthesis.

8. The prosthesis for surgery according to claim 1 in which the groups of holes are placed asymmetrically with respect to the greater dimension of the prosthesis.

9. The prosthesis for surgery according to claim 1, having a length and width ranging between 5 and 300 mm.

10. The prosthesis for surgery according to claim 1, having minimum and maximum dimensions (length×width) ranging between: 20 mm×20 mm, 40 mm×50 mm, 60 mm×80 mm, 80 mm×90 mm, 80 mm×140 mm, 80 mm×160 mm, 80 mm×200 mm, 100 mm×180 mm, 120 mm×200 mm.

11. The prosthesis for surgery according to claim 1, having a rectangular, elliptical or "bean" shape.

12. The prosthesis for surgery according to claim 1 having a rectangular shape with a drainage group placed at the center of the prosthesis.

13. A prosthesis for surgery consisting of animal derived collagen having a peripheral perimeter and a drainage portion within the perimeter provided with a plurality of drainage holes, wherein the holes are placed in one or more groups, and each group has a regular body-centered polygon layout, wherein each group consists of a single hole at a center of the regular body-centered polygon and holes disposed at vertices of the regular body-centered polygon surrounding the single hole, wherein the holes disposed at the vertices are the only holes that surround the single hole, and wherein each group of holes is independent, such that each group does not share any hole with any other group.

14. The prosthesis for surgery according to claim 13 in which the holes have a diameter of 1.5 mm or more, placed at a distance of 1.5 cm or at a greater distance.

15. The prosthesis for surgery according to claim 13 in which the holes have a diameter of 1.5 mm.

16. The prosthesis for surgery according to claim 13 wherein the holes of each group have a body-centered regular hexagon layout.

17. The prosthesis for surgery according to claim 13 in which the groups of holes are placed symmetrically with respect to the center of the prosthesis.

18. The prosthesis for surgery according to claim 13 in which the groups of holes are placed symmetrically with respect to the center of the prosthesis, but without being placed at the center itself.

19. The prosthesis for surgery according to claim 13 in which the groups of holes are placed asymmetrically with respect to the center of the prosthesis.

20. The prosthesis for surgery according to claim 13 in which the groups of holes are placed asymmetrically with respect to the greater dimension of the prosthesis.

21. The prosthesis for surgery according to claim 13, having a length and width ranging between 5 and 300 mm.

22. The prosthesis for surgery according to claim 13, having minimum and maximum dimensions (length×width) ranging between: 20 mm×20 mm, 40 mm×50 mm, 60 mm×80 mm, 80 mm×90 mm, 80 mm×140 mm, 80 mm×160 mm, 80 mm×200 mm, 100 mm×180 mm, 120 mm×200 mm.

23. The prosthesis for surgery according to claim 13, having a rectangular, elliptical or "bean" shape.

24. The prosthesis for surgery according to claim 13 having a rectangular shape with a drainage group placed at the center of the prosthesis.

\* \* \* \* \*